US00PP15023P2

(12) United States Plant Patent
Epstein

(10) Patent No.: US PP15,023 P2
(45) Date of Patent: Jul. 20, 2004

(54) TATARIAN MAPLE TREE NAMED 'GARANN'

(50) Latin Name: *Acer tataricum*
Varietal Denomination: GarAnn

(75) Inventor: Gary Robin Epstein, Fort Collins, CO (US)

(73) Assignee: Plant Select, Fort Collins, CO (US)

( * ) Notice: Subject to any disclaimer, the term of this patent is extended or adjusted under 35 U.S.C. 154(b) by 27 days.

(21) Appl. No.: 10/628,760

(22) Filed: Jul. 28, 2003

(51) Int. Cl.[7] ..... A01H 5/00
(52) U.S. Cl. ..... Plt./224
(58) Field of Search ..... Plt./224, 216

*Primary Examiner*—Bruce R. Campell
*Assistant Examiner*—Annette H Para
(74) *Attorney, Agent, or Firm*—C. A. Whealy

(57) ABSTRACT

A new distinct cultivar of Tatarian Maple tree named 'GarAnn', characterized by its upright, outwardly spreading and rounded plant habit; strong and nearly horizontal branch angles; attractive fall foliage coloration; and vibrant red-colored samara that retain their coloration for about six weeks.

4 Drawing Sheets

Botanical classification/cultivar designation: *Acer tataricum* cultivar GarAnn.

BACKGROUND OF THE INVENTION

The present Invention relates to a new and distinct cultivar of Tatarian Maple tree, botanically known as *Acer tataricum*, and hereinafter referred to by the cultivar name 'GarAnn'.

The new Tatarian Maple tree originated from a cross-pollination of two unidentified selections of *Acer tataricum*, not patented. The new Tatarian Maple tree was discovered and selected as a single plant from the resulting progeny of the cross-pollination by the Inventor in a controlled environment in Fort Collins, Colo. in 1993.

Asexual reproduction of the new cultivar in a controlled environment by softwood cuttings taken in Fort Collins, Colo., has shown that the unique features of this new Tatarian Maple tree are stable and reproduced true to type in successive generations.

SUMMARY OF THE INVENTION

Trees of the cultivar GarAnn have not been observed under all possible environmental conditions. The phenotype may vary somewhat with variations in environment such as temperature and light intensity without, however, any variance in genotype.

The following traits have been repeatedly observed and are determined to be the unique characteristics of 'GarAnn'. These characteristics in combination distinguish 'GarAnn' as a new and distinct cultivar:

1. Upright, outwardly spreading and rounded plant habit.
2. Strong and nearly horizontal branch angles.
3. Attractive fall foliage coloration.
4. Vibrant red-colored samara that retain their coloration for about six weeks.

Plants of the new Tatarian Maple tree are most similar to the parent, the unidentified selections of *Acer tataricum*. However, in side-by-side comparisons conducted by the Inventor in Fort Collins, Colo., plants of the new Tatarian Maple tree differed from plants of the parent selections in the following characteristics:

1. Plants of the new Tatarian Maple tree had stronger branch angles than plants of the parent selections.
2. Samara of plants of the new Tatarian Maple tree retained their coloration about two weeks longer than samara of plants of the parent selections.

Plants of the new Tatarian Maple tree can also be compared to plants of the *Acer tataricum* cultivar Pattern Perfect, not patented. However, in side-by-side comparisons conducted by the Inventor in Fort Collins, Colo., plants of the new Tatarian Maple tree differed from plants of the cultivar Pattern Perfect in the following characteristics:

1. Plants of the new Tatarian Maple tree had more attractive fall foliage coloration than plants of the cultivar Pattern Perfect.
2. Samara coloration of plants of the new Tatarian Maple tree was deeper red, more intense and longer-lasting than samara coloration of plants of the cultivar Pattern Perfect.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Tatarian Maple tree.

The photograph on the first sheet comprises a side perspective view of a typical 12-year old tree of 'GarAnn' grown in the ground in an outdoor nursery in Fort Collins, Colo. during the early summer.

The photograph on the second sheet comprises a side perspective view of the same tree when it was 8 years old in fruit.

The insert photograph on the second page is a close-up view of typical samara of 'GarAnn'.

The photograph on the third sheet comprises a side perspective view of the same tree of 'GarAnn' during the fall.

The insert photograph on the third sheet is a close-up view of typical fall foliage coloration of 'GarAnn'.

The photograph on the fourth page is a close-up view of the branch angle of a typical tree of 'GarAnn'.

DETAILED BOTANICAL DESCRIPTION

In the following description, color references are made to The Royal Horticultural Society Colour Chart, 1995 Edition, except where general terms of ordinary dictionary significance are used. Trees used for the description were about two years from planting and were grown under commercial practice in the ground in an outdoor nursery in Fort Collins, Colo. During the production of the trees average temperatures ranged from −2 to 22° C.

Botanical classification: *Acer tataricum* cultivar GarAnn.

Parentage: Cross-pollination of two unidentified selections of *Acer tataricum*, not patented.

Propagation:

*Type cutting.*—Softwood cuttings.

*Time to initiate roots.*—About three weeks at 20° C.

*Root description.*—Fibrous and freely branching.

Plant description:

*Form.*—Deciduous tree; upright, rounded and outwardly spreading plant habit.

*Plant height.*—Plants will be about 5.5 meters after 12 years.

*Plant diameter.*—Plants will be about 6 meters after 12 years.

*Branching habit.*—Very strong branch angles, lateral branches nearly horizontal; dense and bushy plant habit.

*Lateral branches.*—Internode length: About 5.5 to 7.5 mm. Strength: Strong. Texture: Smooth, glabrous. Color: Young stems: 172A. Mature stems: 201D.

*Foliage description.*—Arrangement: Simple; mostly alternate, occasionally opposite and lobed. Length: About 5 to 10 cm. Width: About 4 to 7 mm. Shape: Broadly ovate. Apex: Acuminate. Base: Cordate. Margin: Doubly serrate. Venation pattern: Pinnate. Texture, upper and lower surface: Smooth, glabrous; somewhat rugose. Color: Summer, upper and lower surfaces: 141B. Winter, upper and lower surfaces: Center, 25B to 15B, towards the apex, 46A.

Flower description:

*Flower type and habit.*—Single flowers arranged in corymbs or long-peduncled panicles. Not freely flowering; flowering non-recurrent.

*Natural flowering season.*—In Fort Collins, Colo., trees flower in early May and flowering continues for about three weeks.

*Inflorescence diameter.*—About 3 to 5 cm.

*Inflorescence length.*—About 2 to 3 cm.

*Flower diameter.*—About 4 to 5 mm.

*Flower buds.*—Diameter: About 2 to 4 mm. Shape: Spherical.

*Petals.*—Quantity: Five per flower in a single whorl. Length: About 2 mm. Width: About 2 mm. Shape: Rounded. Apex: Obtuse. Margin: Entire. Texture, upper and lower surfaces: Smooth; glabrous. Color, when opening and fully opened, upper and lower surfaces: Close to 158D.

*Peduncles.*—Length: About 5.5 to 7 cm. Color: Close to 141C.

*Reproductive organs.*—Stamens: Quantity: Eight per flower. Anther length: Less than 1 mm. Anther color: 158D. Pollen color: 158D. Pistils: Quantity: Two. Pistil length: Less than 1 mm. Stigma color: 158D. Style color: 158D. Ovary color: 158D.

*Fruit.*—Type: Samara. Shape: Winged, wings nearly parallel. Length: About 2.5 to 3 cm. Diameter: About 8 to 10 mm. Color: 45B; color lasts for about six weeks.

*Seed.*—Type: Flat nutlet. Shape: Elliptic. Length: About 5 to 6 mm. Diameter: About 4 to 5 mm.

Disease/pest resistance: Trees of the new Tatarian Maple tree have not been noted to be resistant to specific pathogens and pests common to Tatarian Maple tree.

Weather tolerance: Trees of the new Tatarian Maple tree have been observed to be tolerant to rain, ice, snow and wind and tolerant to temperatures from −2 to higher than 20° C.

It is claimed:

1. A new and distinct cultivar of Tatarian Maple tree named 'GarAnn', as illustrated and described.

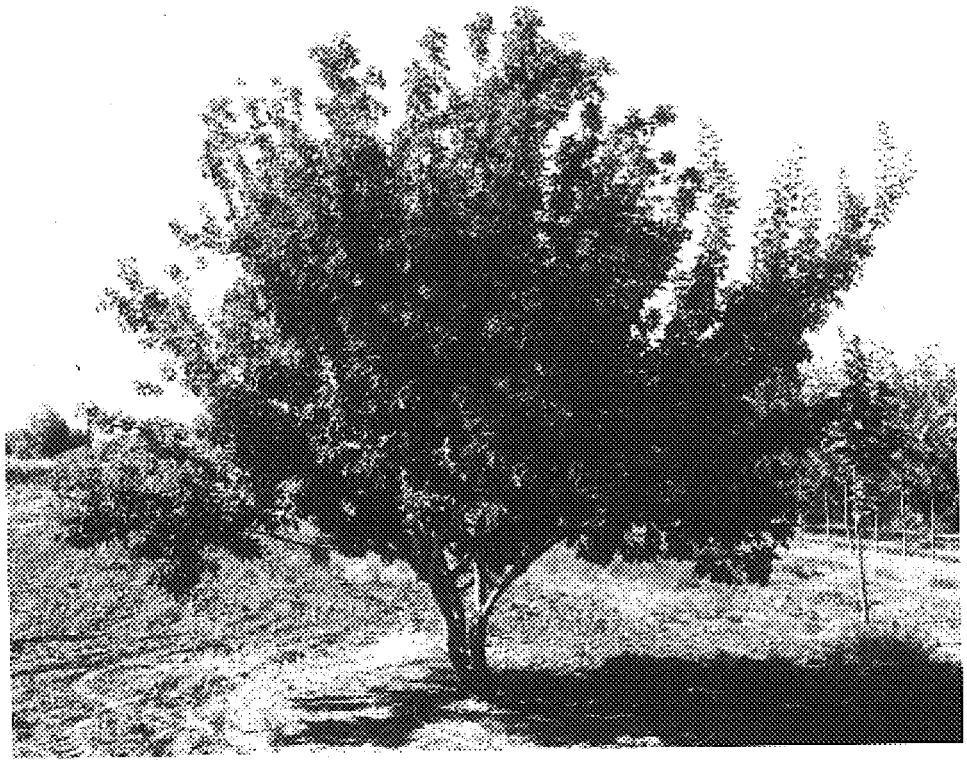

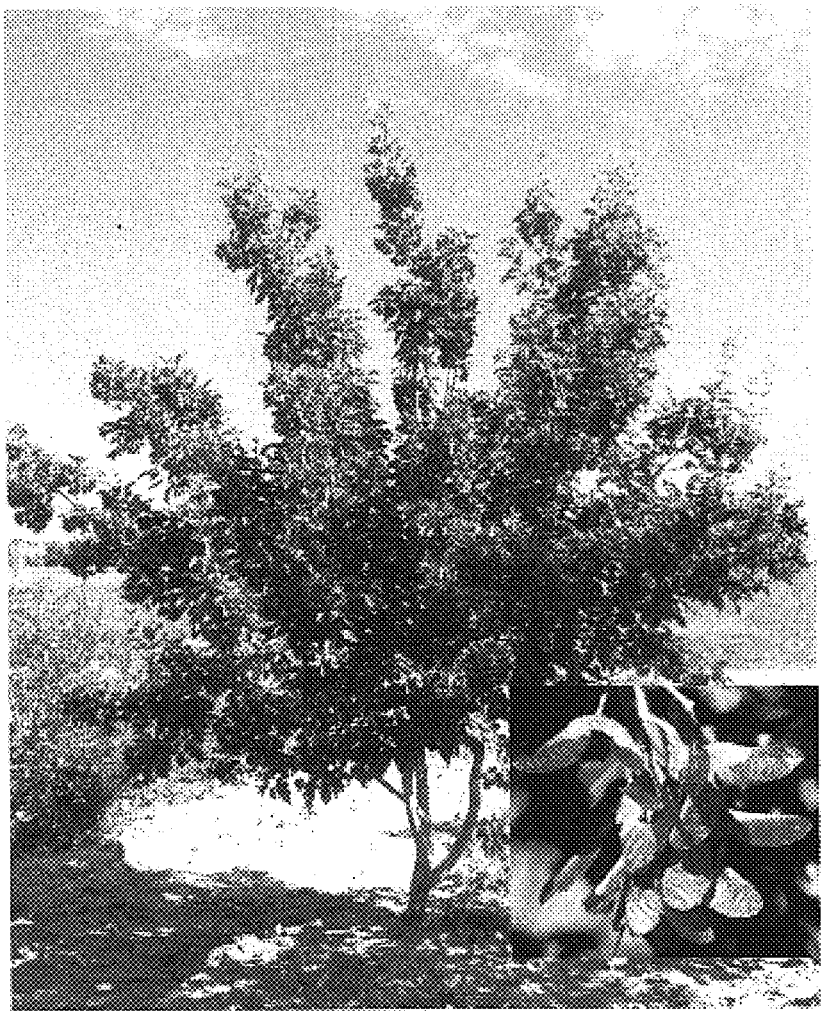

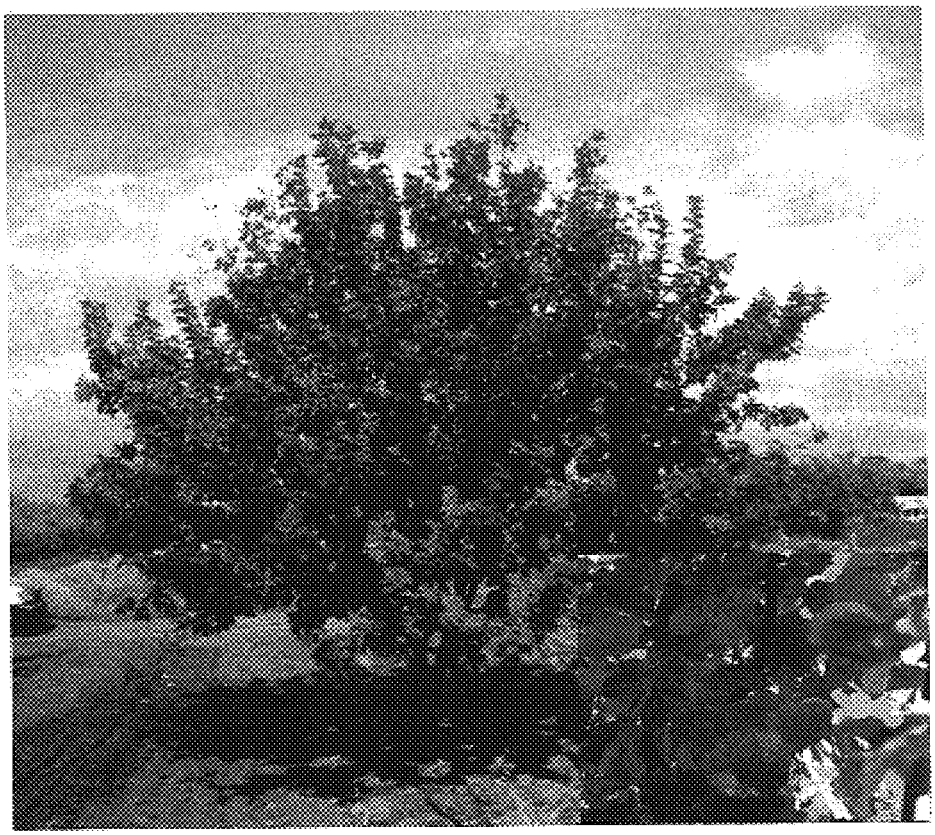

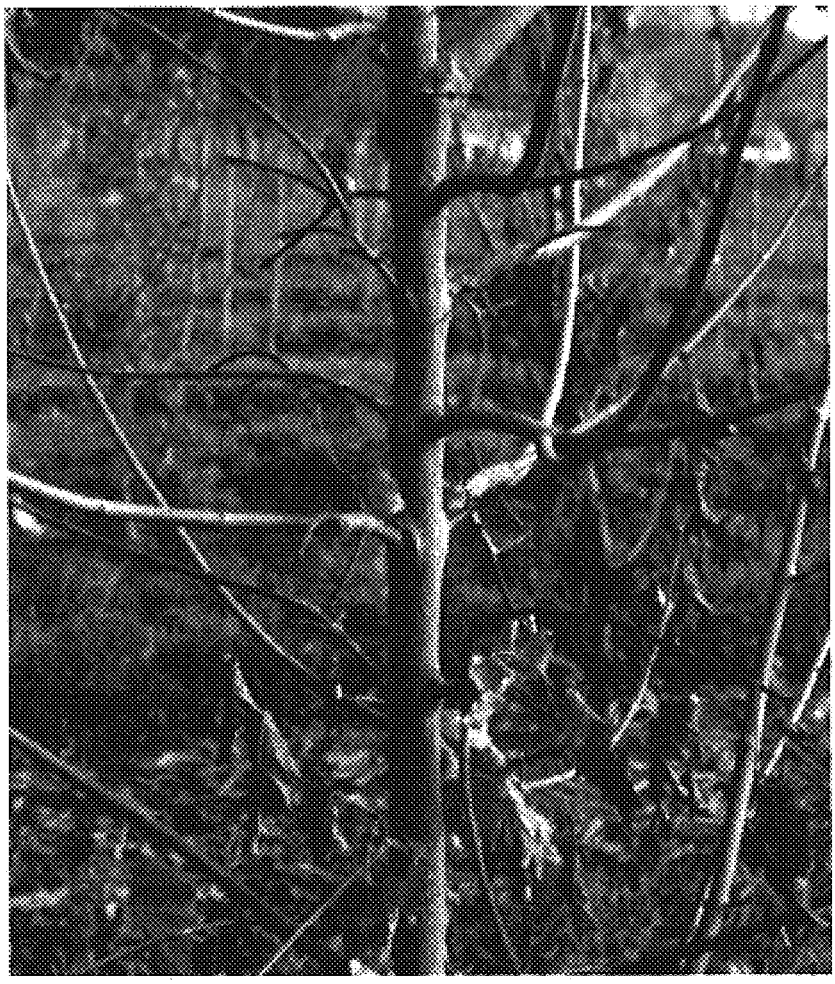

* * * * *